US006946295B2

(12) United States Patent
Polonenko et al.

(10) Patent No.: US 6,946,295 B2
(45) Date of Patent: Sep. 20, 2005

(54) PROCESS FOR EX VITRO SOWING AND GERMINATION OF PLANT SOMATIC EMBRYOS

(75) Inventors: Daniel R. Polonenko, Coquitlam (CA); Eric Evert Voogt, Langley (CA); Potter Ann Kathryn Eastman, Vancouver (CA); Shihe Fan, Vancouver (CA)

(73) Assignee: Cellfor, Inc., Brentwood Bay (CA)

( * ) Notice: Subject to any disclaimer, the term of this patent is extended or adjusted under 35 U.S.C. 154(b) by 233 days.

(21) Appl. No.: 09/330,593

(22) Filed: Jun. 11, 1999

(65) Prior Publication Data

US 2003/0157668 A1 Aug. 21, 2003

Related U.S. Application Data

(60) Provisional application No. 60/089,201, filed on Jun. 12, 1998.

(51) Int. Cl.$^7$ ............................ C12N 5/00; C12N 5/02; A01H 7/00; A01H 3/00; A01G 1/00
(52) U.S. Cl. ................... 435/422; 435/430.1; 435/430; 435/420; 800/319; 47/58.1; 47/57.6
(58) Field of Search ............................. 435/430.1, 430, 435/400, 422; 800/319

(56) References Cited

U.S. PATENT DOCUMENTS

| | | | |
|---|---|---|---|
| 4,583,320 A | 4/1986 | Redenbaugh | |
| 4,777,762 A | 10/1988 | Redenbaugh et al. | |
| 4,780,987 A | 11/1988 | Nelsen et al. | ................. 47/57.6 |
| 4,957,866 A | 9/1990 | Gupta et al. | |
| 5,010,685 A | 4/1991 | Sakamoto et al. | |
| 5,119,588 A | 6/1992 | Timmis et al. | ........... 47/58.1 R |
| 5,183,757 A | 2/1993 | Roberts | |
| 5,183,835 A | 2/1993 | Gross et al. | |
| 5,236,469 A | 8/1993 | Carlson et al. | |
| 5,238,835 A | 8/1993 | McKersie et al. | |
| 5,294,549 A | 3/1994 | Pullman et al. | |
| 5,413,930 A | 5/1995 | Becwar et al. | |
| 5,427,593 A | 6/1995 | Carlson et al. | |
| 5,451,241 A | 9/1995 | Carlson et al. | |
| 5,464,769 A | 11/1995 | Attree et al. | |
| 5,482,857 A | 1/1996 | Gupta et al. | |
| 5,486,218 A | * 1/1996 | Carlson et al. | ............... 47/57.6 |
| 5,491,090 A | 2/1996 | Handley, III et al. | |
| 5,501,972 A | 3/1996 | Westcott | |
| 5,506,136 A | 4/1996 | Becwar et al. | |
| 5,563,061 A | 10/1996 | Gupta | |
| 5,677,185 A | 10/1997 | Handley, III | |
| 5,732,505 A | 3/1998 | Carlson et al. | ............... 47/57.6 |
| 5,771,632 A | 6/1998 | Liu et al. | ..................... 47/57.6 |

FOREIGN PATENT DOCUMENTS

| | | | | |
|---|---|---|---|---|
| EP | 0 327 362 | | 8/1989 | ............ A01N/3/00 |
| EP | 0 608 716 A2 | | 8/1994 | |
| FR | 2748491 | * | 5/1996 | ............ C12N/5/04 |
| FR | 2 748 491 | | 11/1997 | |
| JP | 2-31624 | | 2/1990 | |
| WO | WO 87/01258 | | 3/1987 | ............ A01C/1/06 |
| WO | WO 93/11660 | | 6/1993 | ............ A01H/7/00 |
| WO | WO 94/24847 | | 11/1994 | |
| WO | WO 96/37095 | | 11/1996 | |
| WO | WO 96/37096 | | 11/1996 | |
| WO | WO 98/57536 | | 12/1998 | ............ A01H/4/00 |

OTHER PUBLICATIONS

Fujii et al., In vitro cell dev biol., (1989) 25 (12), 1179–1182.*

Webster, F.B. et al.: "Propagation of interior spruce by somatic embryogensis" Can. J. For. Res., No. 20, 1990, pp. 1759–1765, XP002118327.

Shoemaker et al: "Characterization of somatic embryogenesis and plant regeneration in cotton (*Gossypium hirsutum* L.)" Plant Cell Reports, vol. 3, Jan. 1, 1986, pp. 178–181, XP002094286.

Carlson, W.C. and J.E. Hartle. (1995) Manufactured Seeds of Woody Plants. IN Somatic Embryogenesis of Woody Plants. vol. I. S.M. Jain, P.K. Gupta, and R.J. Newton (Eds.) Kluwer Academic Publishers, Dordrecht, The Netherlands. pp. 253–263.

Gupta, P. and J.A. Grob. (1995) Somatic Embryogenesis in Conifers. IN Somatic Embryogenesis of Woody Plants. vol. I. S.M. Jain, P.K. Gupta, and R.J. Newton (Eds.) Kluwer Academic Publishers, Dordrecht, The Netherlands. pp. 81–98.

Lichter, R. (1982) Induction of haploid plants from isolated pollen of *Brassica napus*. Z. Pflanzenphysiol. 105:427–434.

(Continued)

*Primary Examiner*—Anne Marie Grunberg

(57) ABSTRACT

A multi-step process by which plant somatic embryos can be sown and germinated ex vitro using conventional seeding equipment, growing mixes, and plant propagation environments. The process most preferably comprises the steps of: placing a somatic embryo on or within a three-phase substrate, the phases comprising solid, liquid and gas phases, placing the substrate containing a somatic embryo into an environmentally-controlled plant-growing environment in which at least one environmental factor (i.e. moisture level within the three-phase substrate, atmospheric humidity, temperature, nutrients, ambient light intensity and diurnal photoperiod) may be controlled and manipulated, manipulating at least one of the environmental factors to enable and facilitate germination of the somatic embryo, and applying water and/or nutrient solutions at regular intervals, the intervals preferably ranging from 1 minute–24 hours, to the surface of the substrate in the form of microdroplets, preferably for a period of time ranging between 3 to eight weeks, such that somatic embryo imbibition, germination, growth and development occur. The process can be practiced in non-sterile conditions with "naked" fresh and/or HRHT-treated and/or desiccated embryos, i.e., non-encapsulated or otherwise uncoated embryos, and does not require the use of aseptic techniques or sterilized media or equipment.

38 Claims, No Drawings

OTHER PUBLICATIONS

Roberts, D.R., B.S. Flinn, D.T. Webb, F.B. Webster, and B.C.S. Sutton (1990a) Abscisic acid and indole–3–butyric acid regulation of maturation and accumulation of storage proteins in somatic embryos of interior spruce. Physiol. Plant 78:355–360.

Roberts, D.R., B.C.S. Sutton, and B.S. Flinn (1990b) Synchronous and high frequency germination of interior spruce somatic embryos is achieved following partial drying at high relative humidity. Can. J. Bot. 68:1086–1090.

Sakamoto, Y., N. Onishi, and T. Hirosawa. (1995) Delivery Systems for Tissue Culture by Encapsulation. *IN* Automation and Environmental Control in Plant Tissue Culture. J. Aitken–Christie, T. Kozai, and M.L.A. Smith, Kluwer Academic Publishers, Dordrecht, The Netherlands. pp. 215–243.

Webster, F.B., D.R. Roberts, S.M. McInnis, and B.C.S. Sutton (1990) Propagation of interior spruce by somatic embryogenesis. Can. J. For. Res. 20:1759–1765.

Fujii et al, 1987.*

Fujii et al, 1990.*

Fujii et al, 1992.*

Statement of Opposition against a corresponding application in New Zealand and accompanying pages, dated Feb. 24, 2004.

Fujii, Jo Ann A., et al.; Artificial Seeds For Plant Propagation, Trends In Biotechnology (TIBTECH)—Dec. 1987 [vol. 5], Elsevier Publications, 335–439.

Fujii, Jo Ann A., et al., Alfalfa Somatic Embryo Maturation and Conversion to Plants, Plant Science, 72 (1990) 93–100.

Fujii, Jo Ann A., et al.; Field Planting of Alfalfa Artificial Seeds, In Vitro Cellular & Developmental Biology: Journal of The Tissue Culture Association, 28P, (1992), 73–80.

Frazier, Diamantina C., et al., "Storage of Pregerminated Seed of Snapdragon (*Antirrhinum majus* L.) in Hydrophilic Gels[1]", J. Amer. Soc. Hort. Sci. 107(4):660–664, 1982.

Knowles, N. Richard and Dun, W.W., "Effects of Cultivar and Storage Duration on Emergence and Yield of Fluid–Drilled Pre–germinated Lettuce Seed", Scientia Horticulturae, 31 (1987), 25–33.

Park, Y.S., et al., "Somatic embryogenesis in white spruce (*Picea glauca*): genetic control in somatic embryos exposed to storage, maturation treatments, germination, and cryopreservation", Theor Appl Genet (1994) 89: 742–750.

Ammirato, Phillip V., "Hormonal Control of Somatic Embryo Development from Cultured Cells of Caraway", Plant Physiol, vol. 59, 1977, pp. 579–583, 586.

Fujii, Jo Ann A., et al., "Artificial seeds for plant propagation", TIBTECH, Dec. 1987, vol. 5, pp. 335–339.

Lai, Fang–Ming, et al., "Germination of Alfalfa (*Medicago sativa* L.) Seeds and Desiccated Somatic Embryos", J. Plant Physiol. vol. 145, pp. 507–513 (1995).

Lai, Fang–Ming and McKersie, Bryan D., "Germination of Alfalfa (*Medicago sativa* L.) Seeds and Desisccated Somatic Embryos", J. Plant Physiol. vol. 146, pp. 731–735 (1995).

Database WPI, Section Ch, Week 8802, Derwent Publications Ltd.,, London, GB; Class A97, AN 88–011651, XP002115789 & JP 62 275604 A (Teijin Ltd), Nov. 30, 1987, Abstract.

* cited by examiner

PROCESS FOR EX VITRO SOWING AND GERMINATION OF PLANT SOMATIC EMBRYOS

CROSS-REFERENCE TO RELATED APPLICATIONS

This application claims the benefit of U.S. Provisional Application No. 60/089,201, filed Jun. 12, 1998.

BACKGROUND OF THE INVENTION

1. Field of the Invention

This invention relates to processes for propagating plants. More particularly, the invention relates to processes for handling, sowing, and germinating plant somatic embryos.

2. Description of the Related Art

Considerable attention has been given to the development of somatic embryogenesis processes for clonal reproduction of plants, and consequently, the specific steps of somatic embryogenesis have been documented in the art for a wide diversity of plant species including both gymnosperms and angiosperms. All methods of somatic embryogenesis are known as tissue culture processes and generally commence with the selection of an explant from a desired plant. The explant is removed from the parent plant tissue by excision and is subsequently cultured on at least one medium to produce a cell mass capable of further differentiation and development. The cell mass can be maintained and proliferated in the undifferentiated state indefinitely, or manipulated to stimulate differentiation into immature somatic embryo structures which can then be cultured further into mature embryos (see, for example, U.S. Pat. Nos. 4,957,866; 5,238,835; 5,294,549; 5,491,090; 5,501,972; 5,563,061; 5,677,185, as well as PCT Publication No. WO 96/37096, all of which are hereby incorporated by reference). Matured somatic embryos can be harvested and germinated immediately, or dried and then germinated, or dried and stored until required for germination (for example, refer to U.S. Pat. Nos. 5,183,835; 5,238,835; 5,413,930; 5,464,769, as well as PCT Publication No. WO 96/37095, all of which are hereby incorporated by reference).

Tissue culture media used to proliferate and propagate plant cultures through the various stages of somatic embryogenesis are typically enriched with mixtures of nutrients that are specifically formulated for each plant species and for the various stages of somatic embryogenesis. A common problem encountered with all somatic embryogenesis processes is microbial, i.e., bacterial, fungal, yeast, contamination of the media and/or plant explants and/or the resulting embryogenic cultures. Microbial contaminants compete with the embryogenic cultures for the nutrients in the media, and in many cases will infect, consume, parasitize, or otherwise pathogenize the cultures. Consequently, steps must be taken to prevent microbial contamination from the beginning of the embryogenesis process when the tissue explants are excised from the parent tissues, through production, harvesting, drying and germination of the somatic embryos and their subsequent growth into fully functional transplants, i.e., somatic seedlings which can be transplanted into soil or horticultural growing mixes. All manipulations of the cultures at each step of the somatic embryogenesis processes are typically done using aseptic techniques. Embryogenic cultures which show any evidence of microbial contamination at any step in somatic embryogenesis process are sterilized and discarded.

Two of the greatest barriers to commercializing somatic embryogenesis technologies are the processes of sowing and germinating plant somatic embryos. Although numerous protocols are known for the sowing and germination of somatic embryos and growing them into intact functional seedlings, none of these protocols have demonstrated compatibility with conventional high-volume through-put horticultural equipment and practices.

Generally, the known protocols for germinating somatic embryos fall into two categories. The first is sowing naked, i.e., uncoated, somatic embryos using aseptic techniques, onto sterilized semi-solid or liquid media contained within a solid-support to facilitate germination (e.g., U.S. Pat. Nos. 5,183,757; 5,294,549; 5,413,930; 5,464,769; 5,506,136) and subsequently, transplanting the germinants into conventional growing systems. The most significant disadvantage of such protocols for sowing naked somatic embryos is that each embryo typically must be handled and manipulated by hand for the germination and transplanting steps. Although various automation options including robotics and machine vision, have been assessed for their usefulness in cost-effective reduction or elimination of the extensive hand-handling currently necessary to sow naked embryos (Roberts et al., 1995), no commercial equipment currently exists which can reliably, aseptically, and cost-effectively perform the in vitro protocols for germination of naked somatic embryos and subsequent transplanting into conventional propagation systems The second category of protocols teach encapsulation of somatic embryos (e.g., U.S. Pat. Nos. 4,777,762; 4,957,866; 5,183,757; 5,482,857, all of which are herein incorporated by reference) to provide a means by which the embryos can presumably be sown with mechanical devices such as seeders and fluidized drills, into conventional growing systems. However, there are a number of disadvantages with encapsulated somatic embryos. For example, the hydrated semi-solid physical characteristics of encapsulated embryos make them incompatible for use with conventional seeding equipment currently available for commercial plant propagation, because the semi-solid encapsulated somatic embryos tend to clump together during handling and consequently, are difficult to singulate and dispense. Furthermore, compositions of encapsulated embryos prepared as taught by the art, clog-up the conventional equipment, and for these reasons, it currently is not possible to sow encapsulated embryos with conventional seeding equipment. Consequently, novel equipment has been developed specifically for delivery of encapsulated somatic embryos into conventional growing systems. Such sowing devices have been reviewed by Sakamoto et al. (1995), but these devices have only been developed and tested as prototypes. Because of mechanical limitations and the high costs associated with the prototype mechanical seeders developed for sowing encapsulated embryos, none are currently available for commercial acquisition and use.

Another disadvantage with encapsulated somatic embryos is the lack of nutrient availability that is characteristically supplied to zygotic embryos by their attendant endosperm or megagametophyte tissues. Consequently, the encapsulation technology for somatic embryos has been extended to include the incorporation of various nutrients such as sugars, fertilizers, oxygen, into the encapsulation media (e.g., Carlson & Hartle, 1995; U.S. Pat. Nos. 4,583,320; 5,010,685; 5,236,469, all of which are herein incorporated by reference). However, a distinct disadvantage associated with nutrient-amended encapsulated embryos is their susceptibility to microbial invasion during manufacture, storage, and during germination if germinated on non-sterile media.

Furthermore, it must be pointed out that although considerable prior art (e.g., PCT Patent Application WO 94/24847, and U.S. Pat. Nos. 5,010,685; 5,236,469; 5,427,593; 5,427,593; 5,451,241; 5,486,218) teaches methods to manufacture "artificial seeds" consisting of somatic embryos encapsulated in gels, which may or may not be amended with nutrients, and which may or may not be encased within a rigid covering, and although the prior art makes references to sowing said artificial seeds ex vitro into germination media comprised of soil or soil-less mixes, the prior art only teaches methods for germinating said artificial seeds in vitro, i.e., on sterilized semi-solid laboratory media. No methods are taught in the prior art for sowing said encapsulated somatic embryos and/or manufactured and/or artificial seed into conventional growing systems using conventional sowing equipment.

However, the most significant disadvantage with all prior art taught for encapsulating or otherwise coating somatic embryos, is that somatic embryos processed by the use of those protocols typically have as a consequence, much lower germination vigor and success than corresponding zygotic seeds (Carlson & Hartle, 1995). Carlson and Hartle (1995) concluded that considerable research is still required before "manufactured" or "artificial" seeds based on encapsulation and/or coating of somatic embryos will have practical utility. However, it should be noted that the germination vigor of naked, i.e., uncoated or non-encapsulated somatic embryos produced with methods disclosed in the art can approximate those of corresponding zygotic seeds (e.g., greater than 85%) (Gupta & Grob, 1995).

BRIEF SUMMARY OF THE INVENTION

An object of the present invention is to facilitate the production of seedlings from somatic plant embryos.

It is another object of the present invention to provide a process by which a somatic embryo can be sown and germinated ex vitro, and grown into seedlings using conventional horticultural and agricultural equipment, containers, growing substrates, and growing environments.

Another object of the invention is to provide a process by which the ex vitro sowing and germination of somatic embryos can be applied to a number of diverse gymnosperm and angiosperm species.

These and other objects and advantages are achieved by a novel multi-step process according to the present invention by which somatic embryos can be sown and germinated ex vitro using conventional seeding equipment, into a wide variety of horticultural nursery containers filled with various types of non-sterile growing mixes commonly used in commercial horticultural, forestry and agricultural plant propagation. A significant advantage of the process of the present invention is that it can be practiced in conventional plant propagation growing environments without the need for aseptic handling processes or for sterile growing environments.

According to one aspect of the present invention, there is provided a process for germinating somatic embryos having a period of somatic embryo germination, the process comprising the steps of: placing a somatic embryo on or within a three-phase substrate, the phases comprising solid, liquid and gas phases; placing the substrate containing a somatic embryo into an environmentally-controlled plant-growing environment in which at least one environmental factor may be controlled and manipulated; manipulating the at least one factor to enable and facilitate germination of the somatic embryo, and applying water and/or nutrient solutions at regular intervals during the period of somatic embryo germination, the intervals preferably ranging from 1 minute-24 hours, to the surface of the substrate in the form of microdroplets, for a period of time preferably ranging between 3 to eight weeks, such that somatic embryo imbibition, germination, growth and development occur.

The invention further includes growing such embryos into seedlings, preferably by reducing the volume of water and nutrients applied to the surface of the three-phase substrate as microdroplets during the period of time which the germinated embryos become autotrophic (usually after a period of 3 to 8 weeks from commencement of sowing). There is, of course, no need to halt the process after germination and before development further into fully functional seedlings. The entire process is carried out continuously from initial sowing to production of final seedling product.

The invention also includes germinated embryos and seedlings developed and grown by the above processes.

The process of the invention includes, but is not restricted to, the steps of sowing somatic embryos using conventional seeding equipment, into horticultural containers containing a selected growing substrate, then placing the containers into growing environments wherein one or more environmental parameters comprising temperature, light, humidity, moisture and nutrition, are controlled and manipulated in a manner such that, over a period of time, the somatic embryos proceed to germinate into complete seedlings comprising roots and shoots.

In a preferred form, naked (un-encapsulated) embryos are employed ex vitro in non-sterile growing conditions, supplying water and nutrients exclusively by means of microdroplets to the growing substrate. It is believed that an advantage of the use of microdroplets is that they allow the embryos to remain completely undisturbed during germination. Not only are the embryos physically undisturbed, but there are no rapid changes of temperature or humidity or nutrient concentration around the embryos that could possibly be the case with conventional watering and nutrient feed techniques (i.e. sprinkling, soaking, etc., using liquid flows or large drops).

There are several advantages inherent with the use of the process of the present invention. For example, one advantage is that aseptic procedures, and sterile or sanitized equipment and germination/growing environments are not required for successful germination of somatic embryos and their subsequent development into complete seedlings, thus enabling the entire sowing and germination steps to be performed in commercial greenhouse or nursery growing facilities. Another advantage is that naked (unencapsulated) embryos may be employed. A further advantage is that somatic embryos can be sown with conventional seeding equipment such as, but not restricted to, vacuum-drum seeders or needle-jet seeders. A further advantage is that commonly used horticultural and agricultural products such as, but not restricted to, soil-less seedling mixes or rock wool or foams and the like, can be used as supports onto which somatic embryos are sown and subsequently germinate into and penetrate with their roots.

Yet a further advantage is that if necessitated by the conditions in the commercial growing environments, existing commercial pesticide products such as, but not restricted to, fungicides, bactericides, antibiotics, nematicides, insecticides and the like, which are registered for use with the plant species from which the somatic embryos are produced, can be applied to the sown somatic embryos per label instructions for effective pest control, or alternatively, applied to the growing substrates prior to sowing the somatic embryos. Another advantage is that exogenous nutrients necessary for successful somatic embryo germination can be applied via numerous methods commonly used in commercial horticulture, said methods including but not restricted to misting, fogging, spraying, watering and drenching. Furthermore, said exogenous nutrients can be applied in conjunction with conventional horticultural fertigation practices.

A number of terms are known to have differing meanings when used in literature describing this art. The following definitions are believed to be ones most generally used in the fields of botany, plant somatic embryogenesis, and are consistent with the usage of the terms in the present specification.

An "explant" is the organ, tissue or cells derived from a plant and cultured in vitro for the purposes of starting a plant cell or tissue culture.

An "embryogenic culture" is a plant cell or tissue culture capable of forming somatic embryos and regenerating plants via somatic embryogenesis.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic; a region of embryonal cells subtended by elongated suspensor cells.

The embryonal cells develop into the mature somatic embryo.

A "zygotic embryo" is an embryo derived from the sexual fusion of gametic cells.

"Megagametophyte" is haploid nutritive tissue of gymnosperm seed, of maternal origin, within which the gymnosperm zygotic embryos develop.

"Endosperm" is haploid nutritive tissue of angiosperm seed, of maternal origin, within which the angiosperm zygotic embryos develop.

A "clone" when used in the context of plant propagation refers to a collection of individuals having the same genetic constitution, and are produced from a culture that arises from an individual explant.

A "line" is another term for "clone".

"Nutrients" are the inorganic micro- and macro-minerals, vitamins, hormones, organic supplements, and carbohydrates necessary for culture growth and somatic embryo germination.

"IBA" is indole-butyric-acid, a plant growth regulator.

"NAA" is naphthalene-acetic-acid, a plant growth regulator.

"Imbibition" is the absorption and/or adsorption of water by certain colloids present in seeds or embryos, which results in the swelling of the tissues and activation of enzymatic and physiological processes.

"Germination" is the emergence of a shoot and/or a root from an embryo.

A "microdroplet" is a self-contained unit of liquid (e.g. water or water-based solution) that is smaller than a drop of the same liquid allowed to form by gravity from a nozzle or solid surface, and is generally contained within a collection of similar microdroplets (e.g. a cloud, mist, fog, fine spray, or the like) produced by applying pressure (e.g. air, a gas or a liquid flowing under pressure provided by a pump) to a drop or other body (e.g. a stream) of the liquid. A microdroplet is usually less than half the size (diameter), and may be less than a quarter or tenth of the size, of a drop of the same liquid, and is preferably small enough to remain temporarily suspended in air (i.e. as an aerosol), and to drift with air currents, rather than fall directly to the ground.

"Autotrophic" refers to the stage of plant development when the photosynthetic organelles and related enzymes and biochemical pathways are fully functional and capable of converting light energy, atmospheric carbon dioxide and water into the pre-requisite carbohydrates (e.g., glucose) necessary to sustain further plant growth and development.

DETAILED DESCRIPTION OF THE INVENTION

In a preferred form, the present invention is generally a multi-step process for ex vitro sowing and germination of plant somatic embryos using conventional horticultural equipment and facilities, comprised of but not necessarily restricted to the following sequential steps:

1. Sowing the plant somatic embryos into nursery containers containing a three-phase substrate, said three phases comprising solids, liquids and air.
2. Placing the nursery containers sown with plant somatic embryos, into a conventional plant propagation environment in which light, temperature, atmospheric humidity, and moisture content of the rooting substrate can be controlled and manipulated to enable and facilitate germination of the somatic embryos and their further development into complete seedlings.
3. Supplying an aerosol to the surface of the nursery containers sown with somatic embryos, said aerosol containing the necessary carbohydrate compounds required to initiate and sustain the germination processes of the somatic embryos.
4. Supplying, in the forms of an aerosol and/or a liquid suspension and/or a liquid solution, the micro- and macro-mineral and other nutrative elements required to sustain the germination of somatic embryos and their subsequent development into seedlings.
5. Adjusting as required during the somatic embryo germination period, the ambient light intensity and diurnal photoperiod, temperature and atmospheric humidity to maintain the development of germinated somatic embryos into complete seedlings.

A particular advantage of this novel process, at least in preferred forms, is that special hygienic and/or aseptic and/or sterile handling methods and/or equipment and/or facilities are not required to successfully handle, sow and germinate plant somatic embryos.

It is preferable that the present invention be practiced with plant somatic embryos that have been dried to moisture contents that approximate those of their corresponding zygotic seeds, i.e., in the range of 5–20% and, more specifically, in the range of 10–15%.

However, it is possible to practice the present invention with somatic embryos containing higher moisture contents in the range of 20–78% with the only limitation on the upper limit being the highest level of moisture content that the somatic embryos can be singulated, handled and sown with conventional seeding equipment.

Although the present invention can be practiced with all conventional seeding equipment used for sowing zygotic seeds, it is preferred to use equipment that dispenses seed into multi-chambered nursery containers, commonly referred to as miniplug trays, flats or cell-packs, said containers commonly used to produce plant plugs which can be mechanically transplanted into larger containers or into field-growing environments.

An important advantage of the present invention, at least in preferred forms, is that it can be practiced with a wide variety of non-sterilized growing substrates commonly used in conventional plant propagation. The preferred growing substrate is peat-based and formulated specifically for germination of zygotic seed, and is exemplified by mixtures such as (a) 15.2 cu.ft of peat, 8 cu.ft. of vermiculite, 680 grams of dolomite lime, and 300 grams of Micromax® (a commercial fertilizer composition comprised of microelements such as, but not limited to, sulfur, boron, manganese, magnesium, cobalt and iron), and (b) 16.2 cu.ft. of peat, 6.75 cu.ft. perlite, 4 cu.ft. vermiculite, 6 kilograms of dolomite lime, 1.5 kilograms of gypsum, 375 grams of potassium phosphate, 250 grams micromax, and 35 grams of wetting agent. Alternatively, commercially formulated mixes such as PRO-MIX-G® or PRO-MIX-PGX® (Premier Peat Moss Ltd. Montreal, PQ, Canada—a commercial soilless plant growing media containing, but not limited to, peat, perlite, vermiculite and/or pumice), Sunshine Mix #3 (Sun-Gro Horticulture Inc., Hubbard, Oreg., USA), and Redi-Earth® (The Scotts Co., Marysville, Ohio, USA—a commercial soilless plant growing media containing, but not limited to, peat, perlite, vermiculite and/or pumice), can also be used with the present invention. It is preferred that the peat-based growing substrate is moistened to a moisture content in the range of 50–80% and then dispensed into multi-chambered trays commonly used for commercial production of plant plugs. Although examples of such trays include Styrofoam #252 or #448 miniplug trays manufactured by Beaver Plastics Inc. (Edmonton, AB, Canada) and hard plastic #288 or #512 miniplug trays manufactured by TLC Polyform Inc (Plymouth Minn., USA, 55441), the present invention can be practiced with other types of multi-chambered trays, or alternatively, with individual pots. It should be noted that the practice of the present invention is not restricted to peat-based mixtures, but also includes other substrates such as Jiffy-7 peat plugs, composted or shredded or unprocessed coconut husk fibres commonly referred to as "cor" or "coir" (1993 Crystal Co., St. Louis, Mo., USA), polymerized substrates (Grow Tech Inc., San Juan Bautista, Calif. USA; Preforma Inc., Oberlin, Ohio USA), extruded foams such as Oasis® (Smithers-Oasis Ltd., Kent, Ohio, USA—a commercial expanded foam product comprising urea formaldehyde), rock wool (Rockwool International A/S, Hovedgaden 584, DK-2640, Denmark) and the like. Regardless of the rooting substrate chosen, its physical characteristics should enable development and maintenance of a high relative humidity i.e., in excess of 75% RH, in the gaseous phase within the substrate while minimizing saturation of the substrate with the liquid phase.

After the somatic embryos are sown onto the surfaces of the rooting substrates, if desired, the embryos may be covered with a thin layer of additional rooting substrate that may be comprised of the same material underneath the embryos or, alternatively, with a different type of material. One non-limiting example is sowing embryos onto PRO-MIX-PGX medium, then overlaying the embryos with a thin layer of coir, i.e., composted coconut husk fibres.

Nursery containers sown with somatic embryos are preferentially placed into a conventional plant propagation environment wherein the conditions are within but not limited to the ranges of temperatures of 15–35° C., relative humidities of 75–100%, light intensities of 10–500 foot candles, and diurnal cycles of 6 h day/18 h night to 22 h day/2 h night.

It is preferable to maintain a very high level of atmospheric humidity around the nursery containers sown with somatic embryos, i.e., greater than 90% RH, for the first 2–10 days after sowing to facilitate somatic embryo imbibition and germination. A number of methods can be used to maintain the atmospheric humidity at these levels including but not restricted to placing the containers in a greenhouse environment with misting or fogging equipment which is deployed at controlled intervals, placing the containers in a fogging or misting tent or chamber, placing clear plastic domes over the nursery containers and then removing domes periodically to mist or fog the sown embryos and replacing the domes immediately thereafter. Another non-limiting method is to provide a space ranging between 2 mm and 10 mm above the surface of the rooting substrate onto which the embryos are sown and the top of the container, and then covering the top of the nursery container with a plastic film which is removed to enable misting or fogging of the sown embryos and then immediately replaced. After somatic embryo germination is established as evidenced by development of shoot and root structures, the germinants can be weaned from the high relative humidity environments by gradually reducing the amount of misting/fogging applied and/or by extending the periods of time between the misting or fogging steps.

It is preferable to maintain the sown embryos in a high relative humidity environment, i.e., greater than 90% RH, for a period of, but not restricted to, 3–7 days after sowing to facilitate embryo imbibition, prior to supplying exogenous nutrients required for embryo germination.

Another advantage of the present invention, at least in its preferred forms, is that the exogenous nutrients, including but not restricted to carbohydrates, minerals, vitamins and hormones which are required for successful somatic embryo germination and subsequent growth and development can be applied as aerosols. The nutrient solutions can be applied with, but not restricted to, conventional misting and/or fogging equipment. Although, the nutrients can be applied individually or combined into one solution, it is preferred to supply the carbohydrates as one solution and the remaining nutrients as a separate solution. A non-limiting example of how this can be practiced is by applying a solution containing a sugar source such as but not limited to sucrose in a concentration selected from the non-limiting range of 1.5–9%, preferably in the range of 3–6%, as a mist to the surface of the growing substrate containing a sown embryo, and then applying as a mist at a later time, a solution containing a mixture of mineral nutrients formulated to deliver but not restricted to 454 mg/l nitrogen, 81 mg/l phosphorus, 704 mg/l potassium, 50 mg/l calcium, 39 mg/l magnesium, 193 mg/l sulfur, 3 mg/l manganese, 0.5 mg/l zinc, 89 mg/l chlorine, 3 mg/l iron, 0.7 mg/l iodine, 0.6 mg/l boron, 0.01 mg/l molybdenum, 0.01 mg/l cobalt, and 0.01 mg/l copper. Alternatively, the macronutrients can be supplied as a commercial formulation such as but not restricted to PlantProd® Plant Starter Fertilizer 10-52-10 (nitrogen-phosphate-potassium) or PlantProd® Forestry Seedling Starter 11-41-8 (nitrogen-phosphate-potassium) (Plant Products Ltd., Brampton, ON, Canada). The PlantProd® products are commercial water-soluble fertilizers containing mineral nutrients such as nitrogen, phosphorus and potassium, and a dye.

An alternative non-limited means of supplying exogenous nutrients to somatic embryos sown onto three-phase growing media within nursery containers is to irrigate or "drench" the media with nutrient solutions formulated as previously described. This is preferably done just before the embryos are sown onto the three-phase growing media.

Since microorganisms such as fungi, bacteria, yeast, and algae, are ubiquitous in conventional plant propagation substrates, equipment, containers and growing environments, a wide variety of chemical and biological pesticide products are available to control and eradicate plant pathogens. The inventors of the present invention, however, have surprisingly found that aseptic handling procedures and sterilized growing substrates, nursery containers and environments are not required to successfully germinate and grow plant somatic embryos. Indeed, the present invention can be practiced in conventional plant propagation environments using only the standard commercial methods of hygiene. Furthermore, we have surprisingly found that pesticides such as Benlate® (a commercial fungicide composition containing a chemical active ingredient), Rovral® (a commercial fungicide composition containing a chemical active ingredient), Trumpet® (a commercial insecticide composition containing a chemical active ingredient), and the like, which are registered for pest control in plant crops, can be used on somatic. embryos sown with the novel multi-step procedure of the present invention, without any debilitating effects on germination.

The following Examples are provided to further illustrate the present invention, but are not to be construed as limiting the invention in any manner.

EXAMPLE 1

Somatic embryos (SE) of interior spruce (*Picea glauca engelmannii* complex) line 23–2672 were produced according to the methods of Roberts et al. (1990a; 1990b) and Webster et al. (1990). After harvesting, the SE (somatic embryos) received two drying treatments, the first being HRHT (high-relative humidity treatment) while the second HRHT followed by further drying for 3 days at a relative humidity of 85% (the relative humidity was provided in a sealed chamber containing a saturated KCL solution). The moisture content of SE produced for treatment 1 (HRHT only) was 69.7%, while the moisture content of SE produced for treatment 2 (HRHT followed by RH 85%) was 14.8%. SE from the two drying treatments were hand-sown into phytatrays containing agar comprised of 0.55% Difco Noble Agar, ½ GMD nutrients (Webster et al., 1990), and 2% sucrose. Three phytatrays, each containing 30 SE, were sown with each set of SE (i.e., drying treatments 1 & 2), and then incubated for three weeks at 23° C. with a diurnal cycle of 20 h light and 4 h dark.

A custom-formulated seedling growing mix comprised of 16.2 cu.ft. of peat, 6.75 cu.ft. perlite, 4 cu.ft. vermiculite, 6 kilograms of dolomite lime, 1.5 kilograms of gypsum, 375 grams of potassium phosphate, 250 grams micromax, and 35 grams of wetting agent (WestCreek Farms, Fort Langley, B.C), was prewetted with Benlate suspension (0.5 g/l), then dispensed into a Beaver Plastics Styrofoam miniplug trays containing 252 cells (10 ml/cavity). After the miniplug cells were filled with growing mix, they were dibbled to produce a ¼"–½" head space between the top of the growing mix and the top of the miniplug tray.

SE from the two drying treatments were sown into the miniplug trays (60 SE/treatment/tray). The SE were immediately misted with 2% sucrose and then the miniplug trays were immediately tightly covered with plastic wrap (Saran Wrap). The trays were maintained in a commercial greenhouse environment kept at 20°–25° C. with a 20 h light/4 hr dark diurnal cycle. The SE were misted each morning with 2% sucrose and each afternoon with "plant starter fertilizer formulation at 100 ppm N (PlantProd 10-52-0). The miniplug trays were misted with a Benlate suspension (0.5 g/l) as necessary to prevent fungal growth. The miniplug trays were tightly covered with saran wrap after each misting. Two weeks after sowing, the misting regime was modified to include a commercial rooting hormone formulation (Dip'n Grow®, Astoria-Pacific Inc., Portland Oreg., USA). diluted to deliver 20 ng IBA and 10 ng NAA, Data collected three weeks after sowing, are summarized in Table 1.

TABLE 1

Comparison of in vitro and ex vitro germination of interior spruce somatic embryos.

| | In vitro (1 wk on agar) | | Ex vitro (3 wks in miniplug trays) | |
|---|---|---|---|---|
| | HRHT | HRHT + 85% RH | HRHT 85% RH | HRHT + 85% RH |
| % germination | 97.8 ± 3.6% | 87.8 ± 4.9% | 50.0 ± 8.3% | 71.9 ± 3.8% |

These data demonstrate that SE produced from interior spruce line 23–2672 germinated ex vitro in a non-sterile peat-based growing mix supplemented with exogenous nutrient applications via aerosols, when propagated in a conventional commercial greenhouse facility.

EXAMPLE 2

Somatic embryos (SE) of interior spruce (*Picea glauca engelmannii* complex) line 107–1979 were produced according to the methods of Roberts et al. (1990a; 1990b) and Webster et al. (1990). After harvesting, the SE received two drying treatments, the first being HRHT (high-relative humidity treatment) while the second treatment received HRHT followed by further drying for 3 days in a chamber wherein the atmospheric relative humidity was maintained at 85%. The moisture content of SE produced for treatment 1 (HRHT only) was 64.8%, while the moisture content of SE produced for treatment 2 (HRHT followed by RH 85%) was 42.6%.

Beaver Plastics Styrofoam #252 miniplug trays were filled to within ¼"–½"" of the top of the trays with one of the following soil-less growth substrates:

(1) a custom formulated peat-substrate comprised of 16.2 cu.ft. of peat, 6.75 cu.ft. perlite, 4 cu.ft. vermiculite, 6 kilograms of dolomite lime, 1.5 kilograms of gypsum, 375 grams of potassium phosphate, 250 grams micromax, and 35 grams of wetting agent (WestCreek Farms, Fort Langley, BC, Canada), prewetted with Benlate suspension (0.5 g/l), (2) Oasis foam (Smithers-Oasis Ltd., Kent, Ohio), and (3) Rock Wool (Rockwool International A/S).

Prior to sowing with SE, all substrates were prewetted with a solution containing 2% sucrose, 0.5 g/l Benlate and ½-strength GMD (per Webster et al., 1990). After sowing, the miniplug trays were tightly covered with plastic wrap (Saran Wrap), and misted 3–5 times daily with a solution comprised of 4.5% sucrose and PlantProd Forestry Seedling Starter fertilizer 11-41-8 at 50 ppm N. The miniplug trays were also misted every 2–3 days with a rotation of Benlate, Thiram and Rovral.

Data collected two weeks after sowing, are summarized in Table 2.

TABLE 2

Ex vitro germination success of HRHT-treated interior spruce SE line 107-1917 on various solid substrates in conventional growing systems.

| Growing substrate | % germination | |
|---|---|---|
| | HRHT | HRHT + 85% RH |
| In vitro | | |
| GMD agar | 90% | 73.3% |
| Ex vitro | | |
| Peat-based growing mix | 79.2% | 87.5% |
| Oasis foam | 66.7% | 92.9% |
| Rock wool | 89.3% | 87.5% |

These data demonstrate that SE produced from interior spruce line 107–1917 germinated ex vitro in different types of non-sterile growing substrates including a peat-based formulation, an extruded foam (i.e., Oasis) and rock wool when supplemented with exogenous nutrient applications via aerosols, and propagated in a conventional commercial greenhouse facility,

EXAMPLE 3

Somatic embryos (SE) of interior spruce (*Picea glauca engelmannii* complex) lines 1–1281 and 107–1917 were produced according to the methods of Roberts et al. (1990a; 1990b) and Webster et al. (1990). After harvesting, the SE were dried using the HRHT method.

Beaver Plastics Styrofoam #252 miniplug trays were completely filled with of the following three soil-less growth substrates:

(1) a custom formulated peat-substrate comprised of 16.2 cu.ft. of peat, 6.75 cu.ft. perlite, 4 cu.ft. vermiculite, 6 kilograms of dolomite lime, 1.5 kilograms of gypsum, 375 grams of potassium phosphate, 250 grams micromax, and 35 grams of wetting agent, prewetted with a Benlate suspension (0.5 g/l),
(2) Oasis foam, and
(3) Rock Wool.

Prior to sowing with SE, all substrates were prewetted with a solution containing 2% sucrose, 0.5g/l Benlate and ½-strength GMD (per Webster et al., 1990). After sowing, the miniplug trays were placed into a fogging/misting tent constructed on a greenhouse bench within a commercial greenhouse facility. The miniplug trays were fogged through misting nozzles with a 1-mm orifice (Dramm Co., Manitowoc, Wisc., USA) for 15 secs at 2-hr intervals for 2 weeks. The miniplug trays fogged four times daily through the misting system with a solution comprised of 4.5% sucrose and PlantProd Forestry Seedling Starter fertilizer 11-41-8 at 50 ppm N. The miniplug trays were also misted every 2–3 days with a rotation of Benlate, Thiram and Rovral. Data were collected two weeks after sowing, and are summarized in Table 3.

TABLE 3

Ex vitro germination success of desiccated interior spruce SE lines 1-1281 and 107-1917 on various non-sterile solid substrates.

| Growing Substrate | % germination | |
|---|---|---|
| | Line 1-1281 | Line 107-1917 |
| In vitro | | |
| GMD agar | 58.5% | 56.2% |
| Ex vitro | | |
| Peat-based growing mix | 14.6% | 78.1% |
| Oasis foam | 60.4% | 100% |
| Rock wool | 11.8% | 21.8% |

These data demonstrate that SE produced from interior spruce lines 1–1281 and 107–1917 germinated ex vitro in different types of non-sterile growing substrates including a peat-based formulation, an extruded foam (i.e., Oasis) and rock wool when placed into a conventional misting/fogging tent, and supplemented with exogenous nutrient applications via fogging, and propagated in a conventional commercial greenhouse facility

EXAMPLE 4

Somatic embryos (SE) of interior spruce (*Picea glauca engelmannii* complex) lines 1–1281, 4–2809, 5–1702, 10–1995, 23–2672, 119–2560 were produced according to the methods of Roberts et al. (1990a; 1990b) and Webster et al. (1990). After harvesting, the SE were dried using the HRHT method.

A custom-formulated seedling growing mix comprised of 16.2 cu.ft. of peat, 6.75 cu.ft. perlite, 4 cu.ft. vermiculite, 6 kilograms of dolomite lime, 1.5 kilograms of gypsum, 375 grams of potassium phosphate, 250 grams micromax, and 35 grams of wetting agent 5 (WestCreek Farms, Fort Langley, B.C), was prewetted with a suspension comprised of 3% sucrose, Plant Products Forestry Seedling Starter Fertilizer 11-41-8 at a concentration of 50 ppm N, then dispensed into Styrofoam miniplug trays containing 252 cells (Beaver Plastic Ltd.).

The miniplug trays were sown with SE (1 line/tray), then covered with a thin layer of coir (fine fibres of composted coconut husks) and misted with water. The miniplug trays were then placed into a fogging/misting tent constructed on a greenhouse bench within a commercial greenhouse facility. The miniplug trays were fogged through misting nozzles with a 1-mm orifice (Dramm Co., Manitowoc, Wisc., USA) for 30 sec at 4-hr intervals for 1 week. The miniplug trays were also misted by hand three times daily with a solution comprised of 4.5% sucrose and Forestry Seedling Starter fertilizer 11-41-8 at 50 ppm N. Data collected indicated that average daily temperature within the misting/fogging tent was 25° C. while the average atmospheric relative humidity was 92%.

Data collected one week after sowing, are summarized in Table 4.

TABLE 4

Comparison of in vitro and ex vitro germination of various interior spruce SE lines

| Interior spruce SE line | % germination in vitro (on agar) | % germination ex vitro (in miniplug trays) |
|---|---|---|
| 1-1281 | 67% | 83% |
| 4-2809 | 95% | 85% |
| 5-1702 | 73% | 90% |
| 10-2195 | 68% | 74% |
| 23-2672 | 88% | 89% |
| 119-2560 | 87% | 97% |

These data demonstrate that SE produced from six interior spruce lines sown onto a peat-based growing substrate and covered with a thin layer of coir, germinated ex vitro when placed into a conventional misting/fogging tent, and supplemented with exogenous nutrient applications via fogging, and propagated in a conventional commercial greenhouse facility.

EXAMPLE 5

Somatic embryos (SE) of interior spruce (*Picea glauca engelmannii* complex) line 23–2672 were produced according to the methods of Roberts et al. (1990a; 1990b) and Webster et al. (1990). After harvesting, the SE were dried for three weeks using the HRHT method and then, dried further for 20 h at 23° C. in a sealed chamber containing a RH of 88.5% which was maintained with an unsaturated NaCl solution placed in the chamber. Water contents of embryos were determined immediately after the HRHT treatment, and after the further desiccation at 88.5.% RH. Desiccated embryos were imbibed for 18 h in an environment with a RH of 100%, and then sown into 400-cavity miniplug trays containing a non-sterile peat-based soil-less growing substrate that was gelled with a polymer (Grow Tech Inc., San Juan Bautista, Calif. USA). After sowing was completed, the miniplug trays were placed into a humidified germination chamber for 1 week with the following environmental conditions: 95–98% RH; 25°/20° C. day/night temperatures; a diurnal period of 18 h light/6 h dark; light intensity of 30–40 $\mu M$ $m^{-2}s^{-1}$ photosynthetic photon flux. The blocks were then moved into a misting chamber with similar environmental conditions except for an increase in light intensity to 120–150 $\mu mol$ $m^{-2}s^{-1}$. After two more weeks of growth, germination success was recorded and the results summarized in Table 5.

TABLE 5

Ex vitro germination success of interior spruce line 23-2672 on a non-sterile growing mix gelled with a polymer.

| Spruce line | Embryo water content (%) | | % Germination success |
|---|---|---|---|
| | Post HRHT | Post desiccation | |
| 23-2672 | 56.2 ± 1.7% | 18.2 ± 1.1% | 70.8 ± 4.2% |

These data demonstrate that spruce somatic embryos which were desiccated to water contents approximating those of zygotic spruce seed, germinated when sown directly onto the surface of a non-sterile peat-based growing substrate which had been gelled with a polymer.

EXAMPLE 6

Mature somatic embryos of (1) *Pinus patula* Scheide et Deppe, and (2) western white pine (*Pinus monticola* Doug1. ex D.Don) were directly sown into non-sterile soilless seedling mixes comprised of 50% screened peat and 50% fine perlite (mix B2) in TLC Polyform 288/ml miniplug trays (10 ml/cavity). After sowing, the trays were placed in a humidified growth chamber with an environmental condition of 95–98% RH, day/night air temperatures of 25/20° C., and an 18 hour photoperiod of 90–120 $\mu mol$ $m^{-2}s^{-1}$ photosynthetic photon flux. For the first three days since sowing, a modified GMD nutrient solution containing 3% sucrose was sprayed onto the trays twice a day. Thereafter, nutrient solution application was reduced to only once a day. After 3 weeks, the experiments were terminated and germination successes tabulated. The results are summarized in Table 6.

TABLE 6

Ex vitro germination success with *Pinus patula* and *Pinus moticola* SE.

| Pine species | Line | Soilless growing mix | % Germination success |
|---|---|---|---|
| *Pinus patula* | 168-5074 | 50% peat:50% perlite | 75% |
| | 272-5071 | 50% peat:50% perlite | 80% |
| *Pinus moticola* | 12A-96.6 | 50% peat:50% perlite | 46% |

These data demonstrate that patula pine (*Pinus patula*) and western white pine (*Pinus moticola*) somatic embryos can be directly germinated ex vitro in non-sterile soil-less growing substrates.

EXAMPLE 7

Mature somatic embryos of (1) *Pinus patula* Scheide et Deppe, and (2) western white pine (*Pinus monticola* Doug1. ex D.Don) were directly sown into 400-cavity miniplug trays containing a non-sterile peat-based soil-less growing substrate that was gelled with a polymer (Grow Tech Inc., San Juan Bautista, Calif. USA). After sowing, the trays were placed in a humidified growth chamber with environmental conditions comprised of 95–98% RH, day/night air temperatures of 25/20° C., light intensity of 90–120 $\mu mol$ $m^{-2}s^{-1}$ photosynthetic photon flux and an 18-hour photoperiod. For the first three days since sowing, a modified GMD nutrient solution containing 3% sucrose was sprayed onto the trays twice a day. Thereafter, nutrient solution application was reduced to only once a day. After 3 weeks, the experiments were terminated and germination successes tabulated. The results are summarized in Table 7.

TABLE 7

Ex vitro germination success with *Pinus patula* and *Pinus moticola* SE on a non-sterile growing mix gelled with a polymer.

| Pine species | Line | Soilless growing mix | % Germination success |
|---|---|---|---|
| *Pinus patula* | 168-99 | Polymerized seedling mix | 85% |
| | 168-308 | Polymerized seedling mix | 70% |
| | 168-670 | Polymerized seedling mix | 84% |
| *Pinus moticola* | 12A-96.6 | Polymerized seedling mix | 80% |

These data demonstrate that patula pine (*Pinus patula*) and western white pine (*Pinus moticola*) somatic embryos can be germinated ex vitro in a non-sterile peat-based growing substrate which had been gelled with a polymer.

EXAMPLE 8

Mature somatic embryos of *Pinus patula* Scheide et Deppe and *Pinus patula* were further desiccated for 20 h at 23° C. in a sealed chamber containing a RH of 88.5% which was maintained with an unsaturated NaCl solution placed in the chamber. Western white pine (*Pinus monticola* Dougl. ex D.Don) embryos were desiccated for 72 h in the same environment, i.e., with a RH of 88.5%. Water contents of the embryos were determined immediately after the HRHT treatments, and after the further desiccations at 88.5.% RH. Desiccated embryos were imbibed for 18 h in an environment with a RH of 100%, and then sown into 400-cavity miniplug trays containing a non-sterile peat-based soil-less growing substrate that was gelled with a polymer (Grow Tech Inc., San Juan Bautista, Calif. USA). After the sowings were completed, the miniplug trays were placed into a humidified germination chamber for 1 week with the following environmental conditions: 95–98% RH; 25°/20° C. day/night temperatures; a diurnal period of 18 h light/6 h dark; light intensity of 30–40 $\mu$mol m$^{-2}$s$^{-1}$ photosynthetic photon flux. The blocks were then moved into a misting chamber with similar environmental conditions except for an increase in light intensity to 120–150 $\mu$mol m$^{-2}$s$^{-1}$. After two more weeks of growth, germination successes were recorded and the results summarized in Table 8.

TABLE 8

Ex vitro germination success with desiccated *Pinus radiata*, *Pinus patula* and *Pinus moticola* SE on a non-sterile growing mix gelled with a polymer.

| Pine Species | Line | Embryo water content (%) | | % Germination success |
|---|---|---|---|---|
| | | Post HRHT | Post desiccation | |
| *Pinus patula* | 168-308 | 60.3 + 2.9% | 34.5 + 0.7% | 79% |
| *Pinus radiata* | 21-6763 | 26.3 + 0.8% | 16.7 + 0.8% | 84% |
| *Pinus monticola* | 22M-4572 | n.d* | 31.2 + 2.1% | 74% |

*n.d.: not determined

These data demonstrate that desiccated somatic embryos from various pine species can germinate when sown directly onto the surface of a non-sterile peat-based growing substrate which had been gelled with a polymer.

EXAMPLE 9

Mature somatic embryos of *Pinuspatula Scheide* et Deppe and *Pinus patula* were desiccated for 24 h at 23° C. in a sealed chamber containing a RH of 92.4% which was maintained with an unsaturated NaCl solution placed in the chamber. The embryos were then transferred to a sealed chamber maintained at a RH of 88.5% and further desiccated at 5° C. for 42 h. Water contents of the embryos were determined immediately after the HRHT treatments, and after the further desiccations at 88.5.% RH. Desiccated embryos were imbibed for 18 h in an environment with a RH of 100%, and then sown into 400-cavity miniplug trays containing a non-sterile peat-based soil-less growing substrate that was gelled with a polymer (Grow Tech Inc., San Juan Bautista, Calif. USA). After the sowings were completed, the miniplug trays were placed into a humidified germination chamber for 1 week with the following environmental conditions: 95–98% RH; 25°/20° C. day/night temperatures; a diurnal period of 18 h light/6 h dark; light intensity of 30–40 $\mu$mol m$^{-2}$s$^{-1}$ photosynthetic photon flux. The blocks were then moved into a misting chamber with similar environmental conditions except for an increase in light intensity to 120–150 $\mu$mol m$^{-2}$s$^{-1}$. After two more weeks of growth, germination successes were recorded and the results summarized in Table 9.

TABLE 9

Effects of desiccation process on ex vitro germination of *Pinus patula* and *Pinus radiata* SE.

| Pine Species | Line | Embryo water content (%) | | % Germination success |
|---|---|---|---|---|
| | | Post HRHT | Post desiccation | |
| *Pinus patula* | 168-308 | 69.0 + 2.0% | 31.2 + 1.4% | 45% |
| *Pinus radiata* | B-6722 | 67.1 + 3.1% | 22.2 + 2.4% | 80% |
| | 20-6598 | 64.5 + 0.5% | 19.1 + 0.2% | 70% |

These data demonstrate that desiccated somatic embryos from various pine species can germinate, regardless of how they were processed during desiccation, when sown directly onto the surface of a non-sterile peat-based growing substrate which had been gelled with a polymer.

EXAMPLE 10

HRHT-treated loblolly pine (*Pinus taeda* L) somatic embryos were directly sown into TLC Polyform 288-cavity miniplug trays containing soilless mixes comprised of screened peat and fine perlite. After sowings were completed, the trays were placed in a humidified growth chamber with an environmental condition of 95–98% RH, day/night air temperatures of 26/20° C., and an 18 hour photoperiod with a light intensity of 90–120 $\mu$mol m$^{-2}$s$^{-1}$ photosynthetic photon flux. A modified GMD nutrient solution containing 3% sucrose was sprayed onto the trays once a day. Germination successes were assessed after 2 weeks. The results are summarized in Table 10.

TABLE 10

Ex vitro germination of *Pinus taeda* SE in non-sterile growing mixes.

| Pine species | Line | Soilless growing mix | % Germination success |
|---|---|---|---|
| *Pinus taeda* | G3431 | 50% screened peat, 50% fine perlite | 95.6% |
| | | 60% screened peat, 40% fine perlite | 100% |
| | | 70% screened peat, 30% fine perlite | 99.2% |

These data demonstrate that loblolly pine (*Pinus taeda*) somatic embryos can be germinated ex vitro in non-sterile peat-based growing substrates.

EXAMPLE 11

Matured canola (*Brassica napus* L.) somatic embryos were harvested and conditioned in NLN-13 liquid medium (Lichter, 1982) for one week as follows. Embryos were placed in 250-ml baffled Erlenmeyer flasks containing 100 ml of medium. The flasks were then placed onto a shaker (60 rpm) under constant (24 h/day) illumination at 20–30 $\mu$mol m$^{-2}$s$^{-1}$ of photosynthetic photon flux. The conditioned embryos were then sown into 288-cavity miniplug trays containing non-sterile soilless peat-based seedling mixes. After sowing, the miniplug trays were placed into a high-humidity (95–98% RH) chamber. Photosynthetic photon flux (i.e., light intensity) in the chamber was 30 $\mu$mol m$^{-2}$s$^{-1}$ at the surface height of the trays. A modified GMD solution containing 3% sucrose was sprayed onto the embryos once every weekday during the length of the experiment. Germination success was recorded after 3 weeks. The shoot lengths of the canola somatic seedlings ranged between 0.5 to 4.0 cm tall and their root systems were well developed. The results are summarized in Table 11.

TABLE 11

Effects of germination substrate composition on ex vitro germination of Brassica napus L. SE.

| Growing mix code | Growing mix composition | % Germination |
|---|---|---|
| B1 | 60% fine perlite:60% peat | 46% |
| B2 | 50% fine perlite:50% peat | 33% |
| B3 | 40% fine perlite:60% peat | 17% |
| B4 | 30% fine perlite:70% peat | 53% |
| B5 | 40% coarse perlite:60% peat | 29% |
| B6 | 30% coarse perlite:70% peat | 25% |
| B7 | 50% coarse vermiculite:50% peat | 46% |
| B8 | 40% coarse vermiculite:60% peat | 41% |
| B9 | 25% coarse vermiculite:75% peat | 71% |

These data demonstrate that somatic embryos from an angiosperm species, Brassica napus L., can be directly germinated ex vitro in various compositions of non-sterile soilless growing mixes.

EXAMPLE 12

Matured canola (Brassica napus L.) somatic embryos were harvested and conditioned in NLN-13 liquid medium (Lichter, 1982) for one week as follows. Embryos were placed in 250-ml baffled Erlenmeyer flasks containing 100 ml of medium. The flasks were then placed onto a shaker (60 rpm) under constant (24 h/day) illumination at 20–30 $\mu$mol $m^{-2}s^{-1}$ of photosynthetic photon flux. The conditioned embryos then received a three-day HRHT treatment after which, they were sown into 288-cavity miniplug trays containing non-sterile soilless peat-based seedling mixes. After sowing, the miniplug trays were placed into a high-humidity (95–98% RH) chamber. Photosynthetic photon flux (i.e., light intensity) in the chamber was 30 $\mu$mol $m^{-2}s^{-1}$ at the surface height of the trays. A modified GMD solution containing 3% sucrose was sprayed onto the embryos once every weekday during the length of the experiment. Germination success was recorded after 3 weeks. The results are summarized in Table 12.

TABLE 12

Effects of germination substrate composition on ex vitro germination of HRHT-treated Brassica napus L. SE.

| Growing mix composition | % Germination |
|---|---|
| 30% fine perlite:70% peat | 56% |
| 40% coarse vermiculite:60% peat | 61% |
| 50% fine perlite:50% peat | 40% |
| 40% coarse perlite:60% peat | 86% |

These data demonstrate that somatic embryos from an angiosperm species, Brassica napus L., processed with an HRHT treatment, can be germinated ex vitro in various compositions of non-sterile soilless growing mixes.

EXAMPLE 13

Matured canola (Brassica napus L.) somatic embryos were harvested and conditioned in NLN-13 liquid medium (Lichter, 1982) for one week as follows. Embryos were placed in 250-ml baffled Erlenmeyer flasks containing 100 ml of medium. The flasks were then placed onto a shaker (60 rpm) under constant (24 h/day) illumination at 20–30 $\mu$mol $m^{-2}s^{-1}$ of photosynthetic photon flux. The conditioned embryos then received a three-day HRHT treatment after which, they were further desiccated at 23° C. in one of the following desiccation environments, 84.2% RH; 85% RH; 92.4% RH; 96.7% RH. Water contents of the embryos were determined immediately after the HRHT treatments, and after the further desiccations at 88.5.% RH. Desiccated embryos were imbibed for 18 h in an environment with a RH of 100%, and then sown into 288-cavity miniplug trays containing non-sterile soilless peat-based seedling mixes. After sowing, the miniplug trays were placed into a high-humidity (95–98% RH) chamber. Photosynthetic photon flux (i.e., light intensity) in the chamber was 30 $\mu$mol $m^{-2}s^{-1}$ at the surface height of the trays. A modified GMD solution containing 3% sucrose was sprayed onto the embryos once every weekday during the length of the experiment. Germination success was recorded after 3 weeks. The results are summarized in Table 13.

TABLE 13

Effects of germination substrate composition on ex vitro germination of desiccated Brassica napus L. SE.

| Desiccation treatment | Water content of desiccated embryos | Growing mix Composition | % Germination |
|---|---|---|---|
| 85% RH; 24 h @ 5° C. then 66 h @ 23° C. | 14% | 40% fine perlite: 60% peat | 35% |
| 92.4% RH; 40 h @ 23° C. | 50% | 50% fine perlite: 50% peat | 35% |
| 96.7% RH; 68 h @ 23° C. | 41% | 50% fine perlite: 50% peat | 42% |

These data demonstrate that desiccated somatic embryos from an angiosperm species, Brassica napus L., can be germinated ex vitro in non-sterile soilless growing mixes.

REFERENCES MENTIONED IN THE APPLICATION

1. Carlson, W. C. and J. E. Hartle. (1995) Manufactured Seeds of Woody Plants. IN Somatic Embryogenesis of Woody Plants. Vol. I. S. M. Jain, P. K. Gupta, and R. J. Newton (Eds.) Kluwer Academic Publishers, Dordrecht, The Netherlands. pp. 253–263.
2. Gupta, P. and J. A. Grob. (1995) Somatic Embryogenesis in Conifers. IN Somatic Embryogenesis of Woody Plants. Vol. I. S. M. Jain, P. K. Gupta, and R. J. Newton (Eds.) Kluwer Academic Publishers, Dordrecht, The Netherlands. pp. 81–98.
3. Lichter, R. (1982) Induction of haploid plants from isolated pollen of Brassica napus. Z. Pflanzenphysiol. 105:427–434.
4. Roberts, D. R., B. S. Flinn, D. T. Webb, F. B. Webster, and B. C. S. Sutton (1990a) Abscisic acid and indole-3-butyric acid regulation of maturation and accumulation of storage proteins in somatic embryos of interior spruce. Physiol. Plant 78:355–360.
5. Roberts, D. R., B. C. S. Sutton, and B. S. Flinn (1990b) Synchronous and high frequency germination of interior spruce somatic embryos is achieved following partial drying at high relative humidity. Can. J. Bot. 68:1086–1090.

6. Sakamoto, Y., N. Onishi, and T. Hirosawa. (1995) Delivery Systems for Tissue Culture by Encapsulation. IN Automation and Environmental Control in Plant Tissue Culture. J. Aitken-Christie, T. Kozai, and M. L. A. Smith, Kluwer Academic Publishers, Dordrecht, The Netherlands. pp. 215–243.

7. Webster, F. B., D. R. Roberts, S. M. McInnis, and B. C. S. Sutton (1990) Propagation of interior spruce by somatic embryogenesis. Can. J. For. Res. 20:1759–1765.

What is claimed is:

1. A process of germinating gymnosperm somatic embryos, which comprises:
   (a) ex vitro sowing an unencapsulated gymnosperm somatic plant embryo on or within a non-sterile plant growth medium selected from the group consisting of peat, soil, rock wool, fiber of plant origin, polymer foam and a horticultural growth mix,
   (b) placing the medium containing the somatic embryo into a non-sterile environmentally-controlled plant-growing environment in which relative humidity may be controlled and manipulated,
   (c) maintaining said relative humidity in the range of 90 to 100% for at least two days from sowing to enable and facilitate germination of the somatic embryo, and
   (d) making a nutrient carbohydrate solution available to the embryo, and applying the nutrient solution by a method selected from the group consisting of fogging, misting and irrigation, at least during the period of somatic embryo germination such that somatic embryo imbibition, germination, growth and development occur.

2. A process according to claim 1 wherein the nutrient solution is applied in the form of microdroplets.

3. The process of claim 1 wherein said environmentally-controlled plant growing environment comprises a plurality of environmental factors in addition to said relative humidity and at least one of said environmental factors selected from the group consisting of a moisture level within said growth medium, temperature, nutrients, ambient light intensity and diurnal photoperiod is manipulated during embryo germination to facilitate germination of the somatic embryo.

4. The process of claim 3 wherein said moisture level within said growth medium is maintained in a range of 60–85% during the period of somatic embryo germination.

5. The process of claim 4 wherein said moisture level is maintained in a range of 65–75%.

6. The process of claim 3 wherein the temperature is maintained within a range of 15–37° C. during somatic embryo germination.

7. The process of claim 6 wherein the temperature is maintained within a range of 20–30° C.

8. The process of claim 1 wherein the nutrient solution is applied at intervals within a range of 1 minute to 24 hrs.

9. The process of claim 1 wherein the nutrient solution is applied at intervals within the range of 1 to 7 days.

10. The process of claim 1 wherein the nutrient solution is applied for a period of time ranging from 3 to 8 weeks.

11. The process according to claim 1 wherein the somatic embryo is a somatic embryo which has been previously desiccated to a final moisture content in the range of 5–75%.

12. The process according to claim 1 wherein the growing is a mixture of substrates selected from the group consisting of peat, sawdust, bark chips, wood chips, compost, moss, perlite, vermiculite, pumice, grit, sand, soil, cellulosic fibres of plars origin, extruded foams, extruded fibres, and chemically expanded foams.

13. The process according to claim 1 wherein the growth medium contains a wetting agent.

14. The process according to claim 1 wherein the moisture content of the growth medium is adjusted with water to a range of 60–85% prior to receiving a somatic embryo.

15. The process according to claim 1 wherein the moisture content of the growth medium is adjusted with a nutrient solution to a range of 60–85% prior to receiving a somatic embryo.

16. The process according to claim 1 wherein at least one fungicide to control plant pathogens is incorporated into the growth medium.

17. The process according to claim 1 wherein at least one fungicide to control plant pathogens is applied in liquid form to the growth medium.

18. The process according to claim 1 wherein at least one fungicide to control plant pathogens is applied in aerosol form to the growth medium.

19. The process according to claim 1 wherein at least one insecticide to control plant pests is incorporated into the growth medium.

20. The process according to claim 1 wherein at least one insecticide to control plant pests is applied in liquid form to the growth medium.

21. The process according to claim 1 wherein at least one insecticide to control plant pests is applied in aerosol form to the growth medium.

22. The process according to claim 1 wherein the growth medium is contained within a horticultural container.

23. The process according to claim 22 wherein the horticultural container is a tray containing cells.

24. The process according to claim 23 wherein the tray is a miniplug tray.

25. The process according to claim 22 wherein the horticultural container is a pot.

26. The process according to the somatic embryo placed on or within the growth medium, is covered with a material selected from the group consisting of peat, sawdust, bark chips, wood chips, compost, moss, perlite, vermiculite, pumice, grit, sand, soil, cellulose fibres of plant origin, extruded foams, extruded fibres, and chemically expanded foams.

27. The process according to claim 1 wherein the somatic embryo is placed on or within the growth medium with seeding equipment.

28. The process according to claim 27 wherein the seeding equipment is a vacuum drum seeder.

29. The process according to claim 27 wherein the seeding equipment is a needle jet seeder.

30. The process according to claim 27 wherein the seeding equipment is a fluid drill seeder.

31. The process according to claim 1 wherein the carbohydrate is a sugar selected from the group consisting of monosaccharides and polysatcharides.

32. The process according to claim 1 wherein the carbohydrate is a sugar selected from the group consisting of glucose, fructose, mannose, maltose, and sucrose.

33. The process according to claim 1 wherein only water is applied to the surface of the growth medium for a period of 18–36 hours after sowing the somatic embryo on or within the growth medium, after which time, nutrient solutions are also applied.

34. A process of growing a somatic embryo into a seedling, which comprises maintaining a somatic embryo germinated according to the process of claim 1 in a growth medium, and growing said germinated embryo to develop the germinated embryo into a seedling.

35. The process of claim 34 wherein, as said seedling develops, a nutrient solution is applied at regular intervals to a surface of the growth medium in the form of microdroplets.

36. The process of claim 35 wherein a volume of nutrient solution applied after said embryo has become autotrophic is less than a volume applied before said embryo has become autotrophic.

37. The process of claim 34 wherein no nutrient solution is applied as microdroplets to said embryo after said embryo has become autotrophic.

38. The process of claim 35 wherein said embryo becomes autotrophic within a period of time in the range of 3 to 8 weeks.

* * * * *